United States Patent [19]

Dandliker et al.

[11] Patent Number: 5,434,191
[45] Date of Patent: Jul. 18, 1995

[54] ARTIFICIAL BLOOD CONTAINING PERFLUORO CHEMICALS IN PRESENCE OF EMULSIFYING AGENTS

[75] Inventors: Walter B. Dandliker, La Jolla; W. Keith R. Watson, Alpine; Thomas C. Drees, Flintridge, all of Calif.

[73] Assignee: International Therapeutics Inc., La Jolla, Calif.

[21] Appl. No.: 110,733

[22] Filed: Aug. 23, 1993

Related U.S. Application Data

[63] Continuation of Ser. No. 312,028, Feb. 17, 1989, Pat. No. 5,243,044, which is a continuation-in-part of Ser. No. 899,903, Aug. 25, 1986, abandoned.

[51] Int. Cl.$^6$ ................ A61K 31/025; A61K 31/395
[52] U.S. Cl. ..................... 424/678; 514/183; 514/755; 514/759; 514/833; 514/832; 514/114; 514/267; 540/456; 544/185; 570/130; 424/717; 424/679; 424/680; 424/681
[58] Field of Search ............. 514/832, 183, 755, 759; 540/456; 544/185; 570/130

[56] References Cited

U.S. PATENT DOCUMENTS

| | | | |
|---|---|---|---|
| 2,459,780 | 1/1949 | McBee et al. | 570/130 X |
| 2,490,098 | 12/1949 | Simons | 540/456 |
| 2,519,983 | 8/1950 | Simons | 540/456 |
| 3,730,954 | 5/1973 | Minieri | 544/185 |
| 4,105,798 | 8/1978 | Moore et al. | 514/832 X |
| 4,402,984 | 9/1983 | Moore | 514/832 X |
| 4,604,385 | 8/1986 | Yokoyama et al. | 514/183 |
| 4,605,650 | 8/1986 | Yokoyama et al. | 514/183 |
| 4,654,337 | 3/1987 | Yokoyama et al. | 514/214 |
| 4,859,363 | 8/1989 | Davis et al. | 514/832 X |
| 4,866,096 | 9/1989 | Schweighardt | 514/756 |
| 4,900,824 | 2/1990 | Dandliker et al. | 544/185 |
| 4,917,930 | 4/1990 | McCormick | 514/832 X |
| 5,061,484 | 10/1991 | Heldebrant | 514/832 X |
| 5,068,098 | 11/1991 | Schweighardt et al. | 514/832 X |
| 5,243,044 | 9/1993 | Dandliker et al. | 540/456 |

FOREIGN PATENT DOCUMENTS

| | | | |
|---|---|---|---|
| 0080716 | 6/1983 | European Pat. Off. | 514/832 |
| 58-92680 | 6/1983 | Japan | 514/832 |
| 58-96061 | 6/1983 | Japan | 514/832 |

OTHER PUBLICATIONS

Mellor, J. W. "Comprehensive Treatise on Inorganic and Theoretical Chemistry." vol. II, Supplement I, part 1, pp. 120, 129, 135 Longmans Green and Co., London (1956).
Simons, J. H. Chem. Rev. 8 213 (1931).
Simmons, T. C. et al., J. Am. Chem. Soc. 79 3429 (1957).
Gervasi, J. S. et al., A. Am. Chem. Soc. 78 1679 (1956).
Hazeldine, R. N. J. Chem. Soc. p. 1966 (1950); p. 102 (1951).

*Primary Examiner*—Floyd D. Higel
*Attorney, Agent, or Firm*—William W. Haefliger

[57] ABSTRACT

A blood substitute employs combinations of fluoro or perfluorochemicals capable in the presence of emulsifying agents of forming emulsions stable at room temperature and possessing enhanced oxygen carrying capacity; the invention enables preparation of an improved blood substitute, with improved $O_2$ carrying capacity and stability, as well as lessened anaphylactoid reaction.

8 Claims, No Drawings

ARTIFICIAL BLOOD CONTAINING PERFLUORO CHEMICALS IN PRESENCE OF EMULSIFYING AGENTS

This application is a continuation of Ser. No. 07/312,028 filed Feb. 17, 1989, now U.S. Pat. No. 5,243,044 which is a continuation-in-part of Ser. No. 06/899,903 filed Aug. 25, 1986, now abandoned.

BACKGROUND OF THE INVENTION

This invention relates generally to synthetic blood, and more particularly to an improved blood substitute offering improvements in oxygen carrying capacity and stability, as well as lessened risk of anaphylactoid reaction.

The facile transport of oxygen through Teflon (polyperfluoroethylene) membrane has been well known for many years. The realization of the compatibility of perfluorocarbons with oxygen led to a series of research efforts which subsequently arrived at the utilization of perfluorochemicals as oxygen carriers in a new generation of blood substitutes.

Initial work by Leland Clark of Cincinnati Childrens Hospital, Robert Geyer of Harvard and Henry Sloviter of the University of Pennsylvania, continued and extended by Naito and co-workers, led to a preparation (Fluosol DA 20%) produced for clinical testing by Green Cross of Osaka, Japan. Fluosol DA functioned as an oxygen carrier in animal experiments and showed considerable promise for human use.

However, Fluosol DA* had several significant drawbacks. First, the emulsion of fluorochemical droplets in an aqueous phase was inherently unstable, both thermodynamically and kinetically, necessitating storage of the emulsion in the frozen state. This instability also entailed a laborious and time consuming blending of the emulsion with other accessory solutions immediately before use. As second major problem with Fluosol DA was the \* perfluorodecalin necessity of maintaining the patient on 70 to 100% oxygen to ensure sufficient oxygen supply and exchange in the tissues. Finally, limited clinical experience with Fluosol DA showed an incidence of transfusion reactions and, in order to avoid this problem, led to the pretreatment of patients with steroids in the event a small test dose indicated sensitivity; this type of sensitivity appeared in 3% or less of all cases.

SUMMARY OF THE INVENTION

It is a major object of the invention to provide an improved blood substitute, employing combinations of fluoro or perfluorochemicals capable in the presence of suitable emulsifying agents of forming emulsions stable at room temperature and possessing enhanced oxygen carrying capacity. It is an additional object of the invention to overcome the toxic (anaphylactoid) reaction problem by the use of synthetic phospholipids in the substitute blood in which such fluoro/perfluorochemicals are employed.

DETAILED DESCRIPTION

The solubility of oxygen in fluorochemicals is correlated with the isothermal compressibility of the liquid fluorochemical. The oxygen molecules pack into voids or cavities in the liquid structure in the process of solution, but do not interact significantly with the fluorochemical molecules as evidenced by the quite small enthalpies of solution. In certain of the fluorochemical structures of this invention, the presence of voids or cavities has been intentionally incorporated into the molecular structure. This has been done in two ways, first, by selecting structures which because of their molecular shape pack poorly together and leave voids in the liquid, and second, by building voids or pockets into the molecular structure itself so as to accommodate an oxygen molecule into the interstices of individual fluorochemical molecules.

The fluoro/perfluorochemicals referred to above have structures indicated by the formulas given below. In many of these formulas, only the carbon skeleton of the molecule is shown and it is to be understood that most or all of the remaining valences of the carbon atoms are combined to fluorine atoms to form C—F bonds.

As an illustration, formula (2) shows the totally fluorinated form of hexamethylenetetramine, with $O_2$ molecules in structure voids. $O_2$ is not shown in the other formulas (3)–(16) but it will be understood the $O_2$ molecules can be transported by them, and also within voids or interstices formed by close packing of the structures (2)–(16), a simple illustration being $O_2$ carried in the void formed by three close-packed balls.

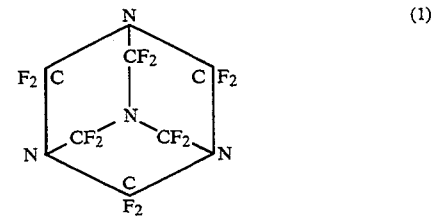

(1) Skeleton formula of perfluoro form of hexamethylenetetramine.

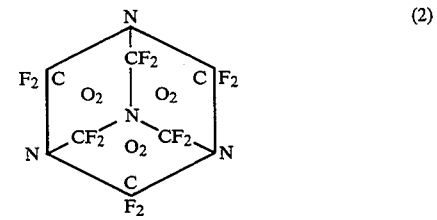

(2) Same as (1), but transporting $O_2$.

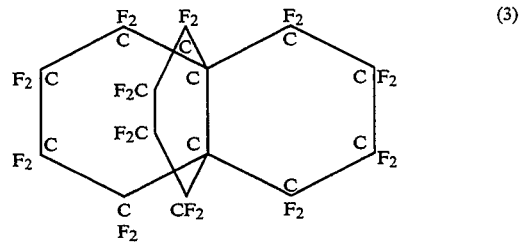

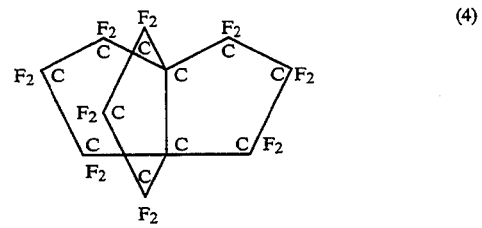

-continued
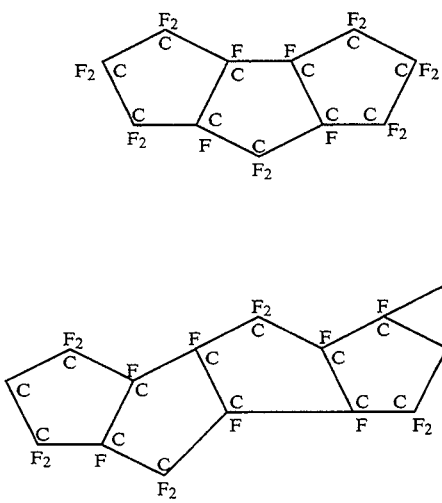 (5)
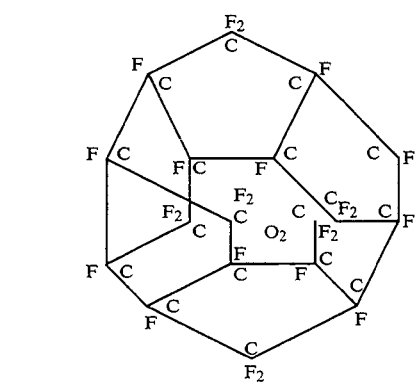 (6)
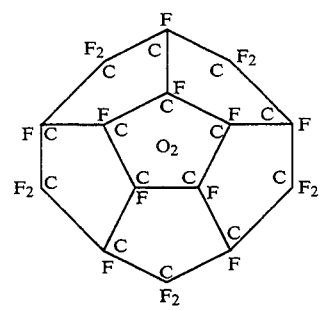 (7)
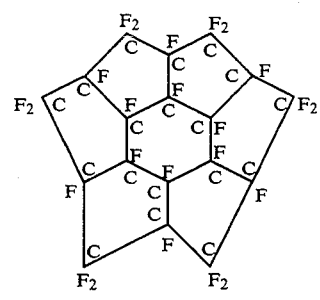 (8)
(9)
-continued
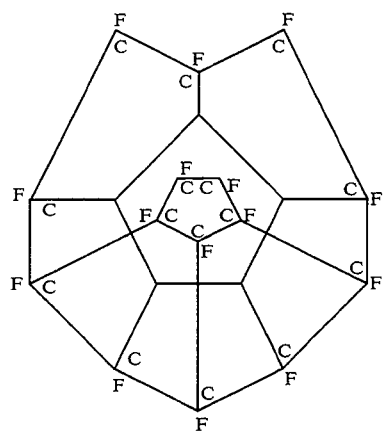 (10)
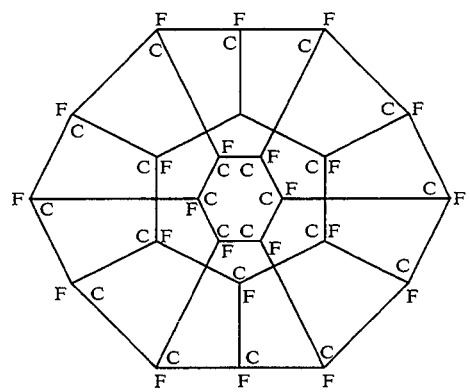 (11)
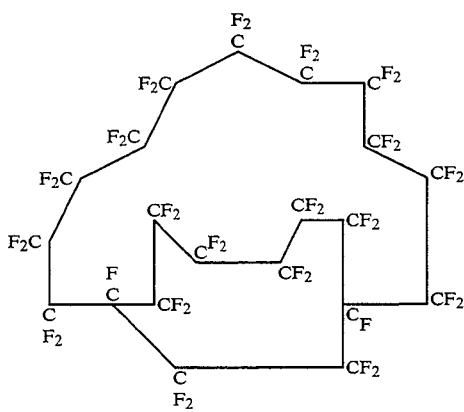 (12)
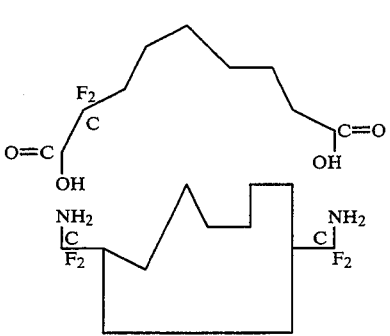 (13)

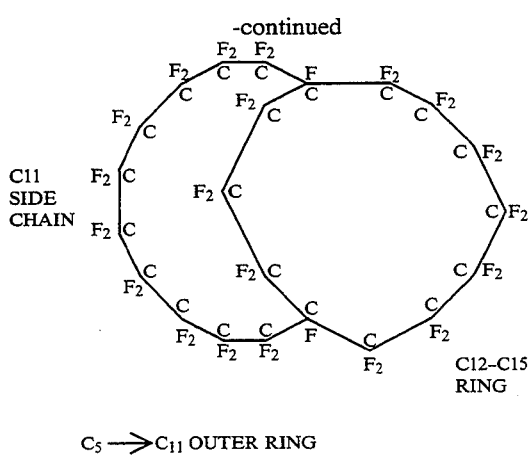

C11 SIDE CHAIN

C12–C15 RING (14)

$C_5 \longrightarrow C_{11}$ OUTER RING

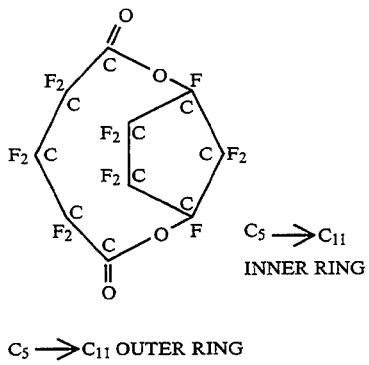

$C_5 \longrightarrow C_{11}$ INNER RING (15)

$C_5 \longrightarrow C_{11}$ OUTER RING

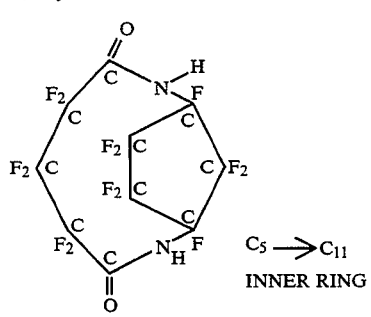

$C_5 \longrightarrow C_{11}$ INNER RING (16)

Such chemicals or mixtures of such chemicals with appropriate surfactants, when emulsified in water along with electrolytes and colloids compatible with natural blood, typically produce droplets which are suspended in solution and which are storable and stable at room temperature, the solution then being directly usable as an oxygen carrying blood substitute. $O_2$ molecules are easily loosely retained for transport in the "basket" areas of the molecules, for example as indicated in (7) and (8) above.

The emulsion contains a non-toxic fraction derived from Pluronic F-68 or equivalent, together with one or more synthetic phospholipids as emulsifiers or surfactants to stabilize the emulsion. The fraction from Pluronic F-68 is prepared by fractional precipitation with organic solvents or salts or by absorption or partition chromatography, starting in either case with commercially available Pluronic F-68. Pluronic F-68* is not a uniform molecular species but instead consists of a mixture of molecules of differing molecular weight. The effectiveness of these different molecular species as emulsifying agents is a function of molecular weight or chain length. It is for this reason that in our process highly refined fractions of optimal molecular weight are used in making the fluorochemical emulsion. In addition, the fractionation employed to prepare these purified materials tends to remove any residual materials toxic to humans or deleterious to red cells. The synthetic phospholipids differ from one another as to whether the overall structure corresponds to that of a lecithin, cephalin, plasmalogen or sphingomyelin and in the \* polyoxyperopylene-polyoxyethylene block co-polymer nature of the fatty acid side chains in the structure. The fatty acids differ in the number of carbon atoms, the number and placement of double bonds and in the presence or absence of alicyclic, aromatic or heterocyclic rings. Synthetic phospholipids, unlike yolk phospholipids contain no trace of egg proteins which in many individuals are highly allergenic. The structure of a typical lecithin is as follows:

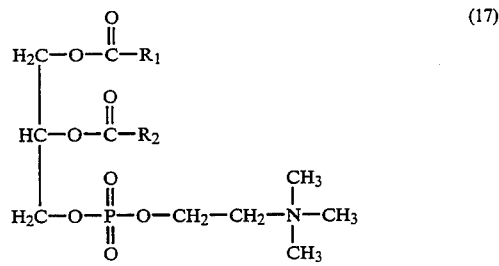

(17)

where $R_1$ and $R_2$ are fatty acids selected from the group stearic acid, linoleic acid, eicosapentaenoic acid and dogosaheyaenoic acid.

In preparing and storing fluorochemical emulsions it is essential to prevent degradative reactions involving any of the components. If such reactions are allowed to occur, emulsion instability and/or toxicity may result.

Several types of such reactions are either known to occur, or may be logically expected to occur, if proper preventive measures are ignored. First, certain fluorochemicals, under the energetic influence of homogenization or sonication, especially in the presence of oxygen, can degrade to yield fluoride ion which is quite toxic. Second, any unsaturation in the fatty acid side chains of the phospholipid emulsifiers may result in the formation of peroxides if oxygen is present and if such reactions are not inhibited. For these reasons, in the present process, oxygen is excluded and, in addition, antioxidants such as vitamin E or other tocopherols are added to provide stabilization for oxygen-labile components.

An emulsion embodying the above described per fluoro compounds prepared for intravenous administration, and also containing a synthetic phospholipid, is as follows:

|  | grams/100 ml. |
|---|---|
| a) Perfluorohexamethylenetetramine | 10–60 |
| b) Perfluoro (3.3.3) propellane | 0.1–50 |
| c) Substance selected from the group consisting of: | about 3.0 |
|    i) hydroxyethylstarch |  |
|    ii) polyvinylpyrolidane |  |
|    iii) modified gelatin |  |
|    iv) dextran |  |
|    v) other polymer to supply colloidal osmotic (oncotic) pressure |  |
| d) Pluronic F-68 fraction | about 2.7 |
| e) Glycerin USP (glycerol) (optional) | about 0.8 (if used) |
| f) NaCl USP | about 0.6 |
| g) Synthetic phospholipids | 0.2–1.0 |
| h) Sodium bicarbonate | about 0.21 |
| i) Dextrose | about 0.18 |

-continued

| | | grams/100 ml. |
|---|---|---|
| j) | Magnesium chloride.6H$_2$O | about 0.043 |
| k) | Calcium chloride.2H$_2$O | about 0.036 |
| l) | Potassium chloride | about 0.034 |
| m) | Water for injection | qs. |

The following are specific examples, with constituents the same as listed above in a)–m):

| Constituents | Examples (gms/100 ml.) | | | | | |
|---|---|---|---|---|---|---|
| | 1 | 2 | 3 | 4 | 5 | 6 |
| a) | 20 | 20 | 25 | 25 | 30 | 30 |
| b) | 40 | 40 | 35 | 35 | 30 | 30 |
| c) | 3.0 | 3.0 | 3.0 | 3.0 | 3.0 | 3.0 |
| d) | 2.7 | 2.7 | 2.7 | 2.7 | 2.7 | 2.7 |
| e) | 0.8 | 0. | 0.8 | 0. | 0.8 | 0. |
| f) | 0.6 | 0.6 | 0.6 | 0.6 | 0.6 | 0.6 |
| g) | 0.4 | 0.4 | 0.4 | 0.4 | 0.4 | 0.4 |
| h) | 0.21 | 0.21 | 0.21 | 0.21 | 0.21 | 0.21 |
| i) | 0.18 | 0.18 | 0.18 | 0.18 | 0.18 | 0.18 |
| j) | 0.043 | 0.043 | 0.043 | 0.043 | 0.043 | 0.043 |
| k) | 0.036 | 0.036 | 0.036 | 0.036 | 0.036 | 0.036 |
| l) | 0.034 | 0.034 | 0.034 | 0.034 | 0.034 | 0.034 |
| m) | qs | qs | qs | qs | qs | qs |

In the above, the synthetic phospholipids are of the structure (17), above.

An increase in molecular weight of fluorochemical is commonly observed to result in an increase in emulsion stability. At the same time, if the fluorochemicals are of too high molecular weight, they are retained for excessive periods of time in the body; and, if the molecular weight is too low, the fluorochemical can form bubbles of vapor within the circulation and can produce enboli. These conflicting factors have led other workers to restrict the useful molecular weight range of fluorochemicals to 460 to 520.

To enable the utilization of the better emulsion behavior of higher molecular weights, the originated fluorochemicals herein maintain their integrity for a relatively short period only—i.e., during the time that supplemental oxygen carrying capacity is needed and subsequently slowly degrade to smaller molecules which are then more easily excreted.

Amidases and esterases are widely distributed in living cells and body fluids. For this reason some of the fluorochemical structures can have amide or ester bonds strategically located so as to provide points of scission when acted upon by amidases or esterases, respectively. In this way large fluorochemical molecules may be used as oxygen carriers with good emulsification properties and still be excreted in reasonable times.

Novel aspects of the invention are as follows:
1. The fluoro or perfluorochemical structures 1 through 17 shown above.
2. Synthetic phospholipids in which the fatty acid chains include those of stearic acid, linoleic acid, eicosapentaenoic acid and dogosaheytaenoic acid.
3. Carrying out the emulsification process under nitrogen or a noble gas to protect labile components of the system from oxidative degradation.
4. Packaging of the final product under nitrogen or a noble gas to protect the product from oxidation during storage.
5. Addition to the product, of vitamin E, mixed tocopherols or other antioxidants compatible with the product and with red cells, to further protect labile components of the mixture against oxidation.
6. Fractions of Pluronic F-68 selected for their superior ability to form and to stabilize emulsions of per fluorochemicals in aqueous solutions compatible with blood.
7. Incorporation of ester or of amide bonds into fluorochemical structures to enable the natural esterases or amidases in blood and tissues to break down the fluorochemical structure by hydrolysis, and to thus decrease the biological half-life of the fluorochemical in the body. This allows the use of fluorochemicals of higher molecular weight which emulsify better to be effectively excreted in reasonable lengths of time.

As regards the molecular form shown at 15, the presence of two

groups will be noted. If we denote the structure to the left of those two groups by "R", and structure to the right by R$_1$ i.e.

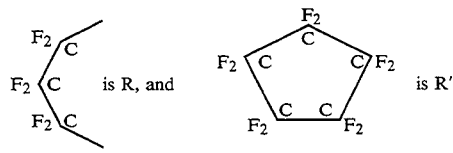

then, in the presence of water, the double chains are hydrolysed, i.e.

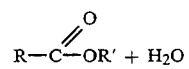

becomes

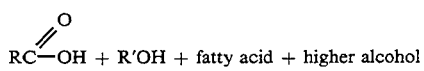

The reason for the two water degradable links is to reduce the molecular weight of the parent molecule, which is large, to two smaller molecular weight decomposition products, i.e. an acid and an alcohol. The parent large molecule is less capable of being expelled (breathed) from the body via the lungs, whereas the two lower molecular weight acid and alcohol products are more readily expelled.

A similar consideration is applicable to the molecular form indicated at (16), where the breakdown links are indicated by the group

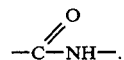

Again,

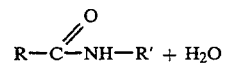

becomes, on hydrolysing,

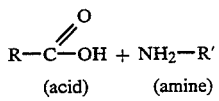

It is important to note that the molecular weight of the artificial blood most ordinarily lies in the range 450–525. Below the 450 level, $O_2$ is not efficiently trapped and has unwanted tendency to "Boil Off". It is also difficult to emulsify. Above the higher molecular weight level, the molecule is too large to be removed from the body, primarily via the lungs. Also, emulsification of small molecules requires excessive surfactant, whereas large molecules emulsify more readily, using less surfactant; therefore larger molecules as shown at (15) and (16) are desirable as they will naturally hydrolyse into smaller molecules, readily eliminated from the body, thereby enhancing emulsification and stability, greater $O_2$ transport, and easier elimination from the body as via the lungs.

Oxygen carriage or transport occurs in two ways, i.e. in the molecular "basket" (see position of $O_2$ in molecular form (8); and $O_2$ entrapment between the molecules, of the forms listed at (2)–(16). Consider the following diagram for example, wherein the perfluoro molecules are denoted by large circles, moving in a capillary, and the oxygen molecules are denoted by dots in the interstices between the large molecules. (Also note the oxygen molecules within the circles, i.e. the first way of $O_2$ transport referred to above).

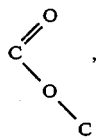

Advantageous results includes greater $O_2$ transport, whereby in-breathing of excessive oxygen by the patient is not required—i.e. the patient can breath ordinary air, exclusively.

The below illustrated (12') modified form of structure (12) above is the same as the latter, except for two "break" locations containing the group

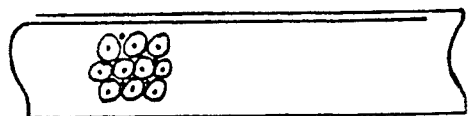

as follows:

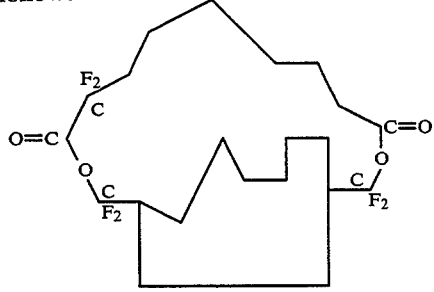

(12')

An alternate form using the "break point" group

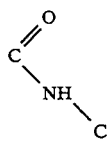

is as follows:

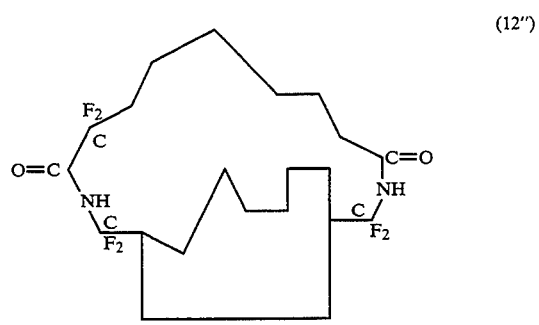

(12")

Similar break point connections are usable for higher molecular weight molecules of the type disclosed herein.

The introduction of fluorine into the various structures shown may be carried out after the molecular skeleton has has been completed or in certain cases before the entire molecule is assembled. As an example of the latter, it may prove preferable in preparing the macrocyclic esters and amides shown to carry out the fluorination before the ester or amide bonds are formed, as for example by an appropriate protective group of alcohol, carboxylic acid or amine to permit fluorination of the methylene groups followed by removal of the protective groups and formation of the ester or amide. Alternatively, the terminal carbons of the constituent chain to be subsequently coupled together can be chlorinated to prevent fluorination of the terminal carbons, the chlorines then later removed by hydrolysis to permit the desired functional group to be introduced.

Fluorination can be accomplished by means of any one of several fluorination reagents or conditions. The exact choice depends upon the degree of fluorination desired, the stability of the carbon skeleton and to a minor degree on convenience and cost.

If it is desired to fluorinate a molecule only partially, then chlorine may be substituted into locations where fluorine is not desired; thereafter, the chlorine is replaced by hydrogen by means of reduction leaving the fluorination intact.

To fluorinate the structures shown requires powerful fluorinating agents such as fluorine itself at very low temperatures either added directly or produced by the electrolysis of hydrogen fluoride. Somewhat milder reagents such as xenon hexafluoride are useful in the first stages of fluorination followed gradually by perfluorinaton or near perfluorination by a more potent reagent.

EXAMPLE

Following perfluorination procedures known in the literature (see references 1) to 7) on page 24e), a stream of liquid hydrofluoric acid, at a density of about 0.9 and at temperatures between −40° C. and 19.0° C. preferably about 0.0° C. is continuously fed into a reaction vessel. Also fed to the vessel is a stream of the "amine"

(i.e. readily available hexamethylenetetramine), in finely divided, solid form. The feed rates are such that chemically equivalent amounts of the acid and amine are fed, per unit time, to the reaction vessel, and on a continuous basis. The reactants in the vessel are stirred and the amine particles are allowed to dissolve. The solution thus formed in the vessel is continuously electrolyzed at a voltage of about 6 volts, using an anode of Ni, and a cathode of carbon. The perfluorinated product resulting from the electrolysis has a density of above 1.5, and collects as a liquid at the bottom of the vessel, below the zone of stirring and electrolysis, and such product, perfluorohexamethylenetetramine, is withdrawn from the bottom of the vessel, on a continuous or semi-continuous basis. Any evolution of $F_2$ is withdrawn from the upper region of the vessel above the solution.

The compound, perfluoro (3.3.3) propellane has been disclosed as an oxygen carrier.

Synthetic methods for obtaining propellanes have developed rapidly over the last decade since the first definitive works in this area appeared (Ginsburg, D., Propellanes, Verlag Chemie (1975); Greenberg, A. and Liebman, J. F., Academaic Press, New York (1978)).

The synthesis of the present compound proceeds in three stages:
1. Formation of the [3.3.3] diketone.
2. Removal of the two keto groups.
3. Perfluorination.

The first step is accomplished by condensation of an acetone dicarboxylic ester with 1,2-diketocyclopentane. The reaction proceeds smoothly at pH 5 in water:

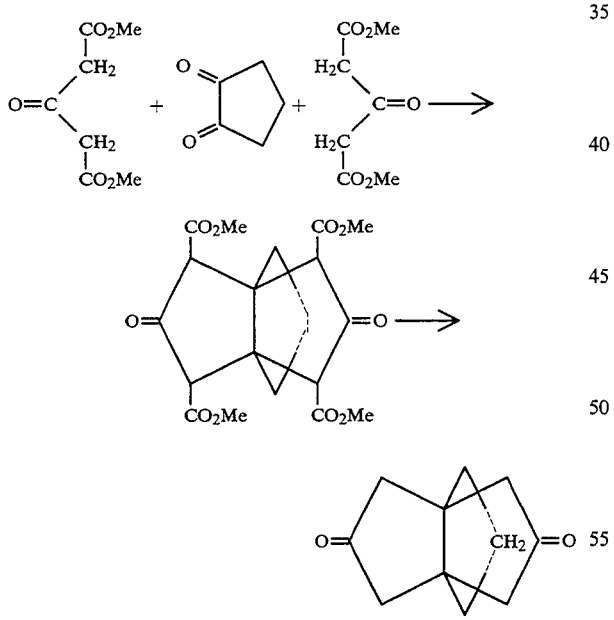

The second step is accomplished by the Wolff Kishner reaction in DMSO (dimethyl sulfoxide) at about 100° C., or by a vapor phase, photochemically activated U.V. reaction. In this reaction one may use either activation with Hg vapor at 2537 Å or to activate at the wavelength of maximum absorption of the hydrazone group. The thermodynamic driving force for this reaction may be attributed largely to the large positive free energy of formation of hydrazine.

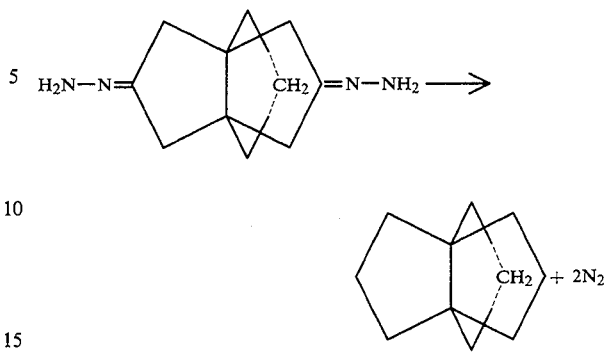

The perfluorination is carried out by the procedure used in the synthesis of perfluorohexamethylenetetramine.

1. Mellor, J. W. Comprehensive Treatise on Inorganic and Theoretical Chemistry, Supplement II, part 1, pp. 120, 129. 135. Longmans Green and Co., London (1956).
2. Simons, J. H. Chem. Rev. 8 213 (1931).
3. Simons, J. H. U.S. Pat. No. 2,519,983 (Aug. 22, 1950).
4. Simons, J. H. U.S. Pat. No. 2,490,098 (Dec. 6, 1949).
5. Simmons, T. C., et al., J.Am. Chem. Soc. 79 3429 (1957).
6. Gervasi, J. A., et al., J.Am. Chem. Soc. 78 1679 (1956).
7. Hazeldine, R. N. J.Chem. Soc. pg 1966 (1950); pg. 102 (1951).

We claim:

1. An artificial blood comprising an emulsion of the following compound in water, said emulsion containing a non-toxic emulsifier and a synthetic phospholipid

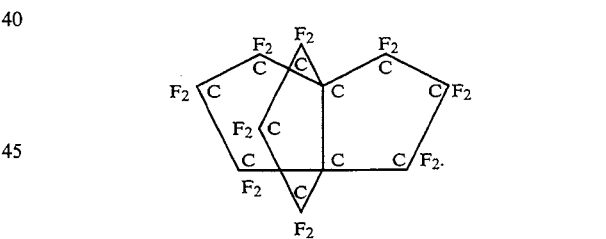

2. An artificial blood comprising an emulsion of the compound

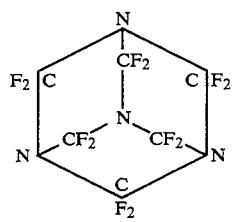

in water, said emulsion containing a non-toxic emulsifier and a synthetic phospholipid, the amount of said compound being 10–60% by weight of the emulsion.

3. The composition of claim 2 wherein said synthetic phospholipid is between 0.2 and 1.0% by weight of the emulsion.

4. The composition of claim 3 wherein the synthetic phospholipid consists of a tri-hydric alcohol esterified with phosphorylcholine.

5. The composition of claim 3 wherein the synthetic phospholipid has the following structure:

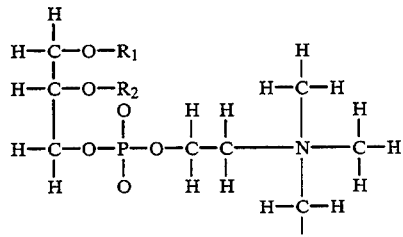

where $R_1$ and $R_2$ are fatty acids.

6. A synthetic blood having the following composition:

|  | grams/100 ml |
| --- | --- |
| a) perfluoro hexamethylenetetramine | 10–60 |
| b) perfluoro [3,3,3] propellene | 0.1–50 |
| c) substance selected from the group consisting of: | about 3.0 |
| i) hydroxyethylstarch | |
| ii) polyvinyl pyrolidane | |
| iii) modified gelatin | |
| iv) dextran | |
| v) other equivalent polymer to supply colloidal osmotic (oncotic) pressure | |
| d) Pluronic F-68 fraction (or equivalent) | about 2.7 |
| e) Glycerin USP (Glycerol) (Optional) | about 0.8 (if used) |
| f) NaCl USP | about 0.6 |
| g) synthetic phospholipid | 0.2 to 1.0 |
| h) sodium bicarbonate | about 0.21 |
| i) Dextrose | about 0.18 |
| j) magnesium chloride.6H$_2$O | about 0.043 |
| k) calcium chloride.2H$_2$O | about 0.036 |
| l) potassium chloride | about 0.034 |
| m) water for injection | qs. |

7. The blood of claim 6, free of glycerin.

8. The blood of claim 6 wherein a) and b) have the following values
a) about 20
b) about 20.

* * * * *